United States Patent [19]

Beck

[11] Patent Number: 4,717,670

[45] Date of Patent: Jan. 5, 1988

[54] PORCINE BETA FSH

[75] Inventor: Anton K. Beck, Chestnut Hill, Mass.

[73] Assignee: Integrated Genetics, Inc., Framingham, Mass.

[21] Appl. No.: 921,867

[22] Filed: Oct. 20, 1986

Related U.S. Application Data

[63] Continuation of Ser. No. 618,466, Jun. 8, 1984.

[51] Int. Cl.⁴ .................. C12N 1/00; C12N 15/00; C12P 21/00; C07H 15/12
[52] U.S. Cl. .................................... 435/320; 435/68; 435/70; 435/172.3; 935/13; 935/60; 536/27
[58] Field of Search ............... 435/68, 70, 91, 240, 435/253, 172.3, 317; 536/27; 935/11, 29, 32, 34, 38, 51, 52, 60

[56] References Cited

PUBLICATIONS

Pavlakis et al. (1982), *PNAS*, vol. 80, pp. 397–401.
Grosveld et al. (1981), *Gene*, vol. 13, pp. 227–237.
Pierce et al. (1981), *Ann. Rev. Biochem.*, vol. 50, pp. 465–495.
Fiddes et al. (1980), *Nature*, vol. 286, pp. 584–587.
Closset et al. (1978), *Eur. J. Biochem.*, vol. 86, pp. 115–120.
Jaye et al. (1981), *Nucleic Acids Res.*, vol. 11, pp. 2325–2335.

*Primary Examiner*—Thomas G. Wiseman
*Assistant Examiner*—Stephanie Seidman

[57] ABSTRACT

A cDNA sequence encoding porcine beta FSH.

3 Claims, 2 Drawing Figures

PORCINE BETA FSH

This is a continuation of co-pending application Ser. No. 618,466 filed on June 8, 1984.

BACKGROUND OF THE INVENTION

This invention relates to fertility hormones produced by recombinant DNA techniques.

Mammals, including humans, secrete several fertility hormones, e.g., leuteinizing hormone (LH) and follicle stimulating hormone (FSH), which are heterodimeric and, within a species, share a common alpha chain, the beta chain of each conferring specificity. It is also known that the FSH of a number of mammalian species is similar enough so that administration of FSH obtained from the pituitary gland of one species is biologically effective in another. Porcine FSH has been shown to induce superovulation in cattle, pigs, sheep, and horses.

SUMMARY OF THE INVENTION

In general, the invention features, in one aspect, a cDNA sequence encoding porcine beta FSH.

In another aspect, the invention features a vector, preferably a plasmid, containing a DNA sequence encoding porcine beta FSH.

The invention can permit the production of highly purified porcine beta FSH, without contamination from LH or other hormones.

The cDNA of the invention is superior to genomic porcine beta FSH DNA because the cDNA does not include untranslated introns, and therefore can be more easily used in prokaryotic host cells.

Other features and advantages of the invention will be apparent from the following description of the preferred embodiments thereof, and from the claims.

DESCRIPTION OF THE PREFERRED EMBODIMENTS

The drawings will first be described.

DRAWINGS

PORCINE BETA FSH cDNA

Figure 1:
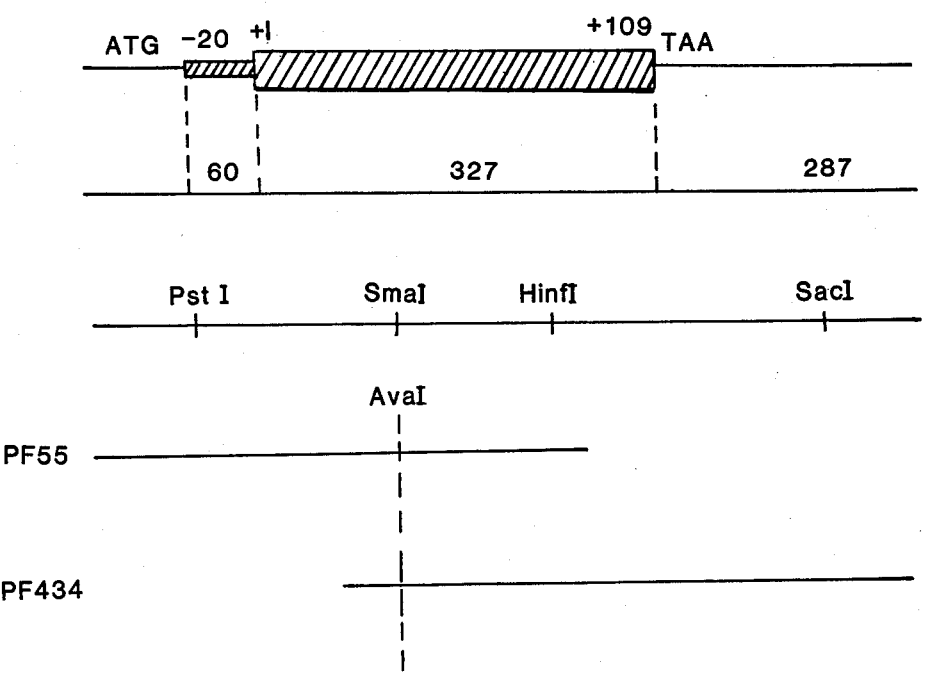
FIG. 1 is a diagrammatic representation of the porcine beta FSH gene, including flanking regions, showing unique restriction sites, and illustrating two DNA regions which were fused to form the complete porcine beta FSH coding sequence.

Table 1 shows the nucleotide sequence which has been determined for the porcine beta FSH cDNA of the invention. The numbers indicate numbers of base pairs; the initial 53 flanking, non-coding base pairs are not given. The initial (5') base pairs shown in Table 1 are untranslated. There is a box around the ATG (bases 108-111) which begins the leader sequence, which is cleaved post-translationally. The mature protein begins with the amino acid Cys encoded by the circled triplet TGT, bases 169-171. There is a box around base numbers 494-496, TAA, the end of the coding region.

Table 2 is the sequence of Table 1, not broken into triplets, showing restriction sites; the ATG beginning the coding region is boxed.

The coding sequence of Tables 1 and 2 encodes porcine beta FSH whose amino acid sequence differs in a number of respects from that which has been published in Closset et al. (1978) Eur. J. Biochem. 86: 115. The differences are summarized in Table 3.

The first step in the production of porcine beta FSH cDNA was to remove the pituitary glands from pigs 20-30 minutes after death. Next, total RNA was extracted, as follows. Homogenization of the tissue was carried out in a 1:1 mixture of phenol:100 mM Na-acetate (pH 5.5) containing 1 mM EDTA, warmed to 60°, for 20 min. After cooling on ice for 10 min., the phases were separated by centrifugation. The hot phenol extraction was repeated twice more followed by two extractions with chloroform.

RNA was precipitated from the final aqueous phase by the addition of 2.5 volumes of ethanol.

In order to enrich for poly A+ mRNA, RNA was passed over oligo (dT)-cellulose in 0.5M NaCl buffered with 10 mM Tris-HCl, pH 7.5, and washed with the same solution. Poly A+ mRNA was eluted with 10 mM Tris-HCl (pH 7.5), 1 mM EDTA, 0.05% SDS, and precipitated twice with ethanol.

A porcine beta FSH cDNA library was constructed by reverse transcription of pituitary mRNA, second strand synthesis using E. coli DNA polymerase I (large fragment), treatment with SI nuclease, and homopolymer tailing (dC) with terminal deoxynucleotidyl transferase; all such procedures were by conventional techniques.

The cDNA molecules were then annealed to DNA fragments of the plasmid pBR322, which had been digested with PstI, and to which dG "tails" have been added. These recombinant plasmids were then used to transform E. coil cells to generate a cDNA library (transformed cells were selected on the basis of tetracycline resistance).

The cDNA library was then screened using "guessed" long probes; the basic concept of such probes, set forth in Jaye et al. (1983) Nucleic Acids Research 11 (8), 2325, is that, if the amino acid sequence of a desired protein is at least partially known, a long probe can be constructed in which educated guesses are made as to the triplet encoding any amino acid which can be encoded by more than one and not more than four different triplets. Any correct guesses increase the amount of homology, and improve the specificity, of the results. To obtain desired regions of cDNA, two labeled 45-mer probes were used: TB36, homologous with amino acids 56-70 of porcine beta FSH, and TB21, homologous with amino acids 72-87. These probes have the following nucleotide compositions (corresponding amino acids are also given):

```
TB36       Val — Tyr — Glu — Thr — Val — Lys —
(AA56-70)  3' CAC  ATG  CTC  TGG  CAC  TCT
           Val — Pro — Gly — Cys — Ala — His —
           CAC  GGT  CCG  ACG  CGG  GTG
           His — Ala — Asp
           GTG  CGA  CTG 5'

TB21       Tyr — Thr — Tyr — Pro — Val — Ala —
(AA72-87)  3' ATG  TGC  ATG  GGT  CAC  CGA
           Thr — Glu — Cys — His — Cys — Gly —
           TGT  CTC  ACA  GTG  ACG  CCG
```

-continued

Lys — Cys — Asp
TTT ACG CTG 5'

The above probes were used to screen the cDNA library as follows. The probes were labeled with ³²P and used to screen the cDNA library by the colony hybridization procedure of Grunstein et al. (1975) PNAS USA 72, 3961. The prehybridization solution was maintained at 55° C. and had the composition: 0.75M NaCl; 0.15M Tris HCl, pH 8.0; 10mM EDTA; 5× Denhardt's Solution; 0.1% sodium pyrophosphate; 0.1% SDS; 100 g/ml E. coli t-RNA. The hybridization solution had the same composition, except that it was maintained at 42° C., and contained probe in a concentration of about 0.5×10⁶ cpm/ml.

The hybridization screening procedure yielded two cDNA sequences, PF55 and PF434, shown in FIG. 1, which also illustrates their relationship with the entire porcine beta FSH sequence. The two sequences were cut with AvaI, which cuts at the unique SmaI site, and fused to form the complete porcine beta FSH clone, with untranslated flanking regions. The cDNA sequence, inserted into the E. coli plasmid pBR322, has been deposited in the Agricultural Research Culture Collection (NRRL), Peoria, IL. and given NRRL Accession Number B-15793. It is agreed that, upon issuance of a patent on this application, all restrictions on availability of the deposited plasmid will be irrevocably removed, and that the plasmid will be maintained throughout the life of the patent.

INSERTION INTO AN EXPRESSION VECTOR

The porcine beta FSH cDNA sequence of the invention can be inserted, using conventional techniques, into any of a variety of expression vectors, for the production of porcine beta FSH.

Figure 2:
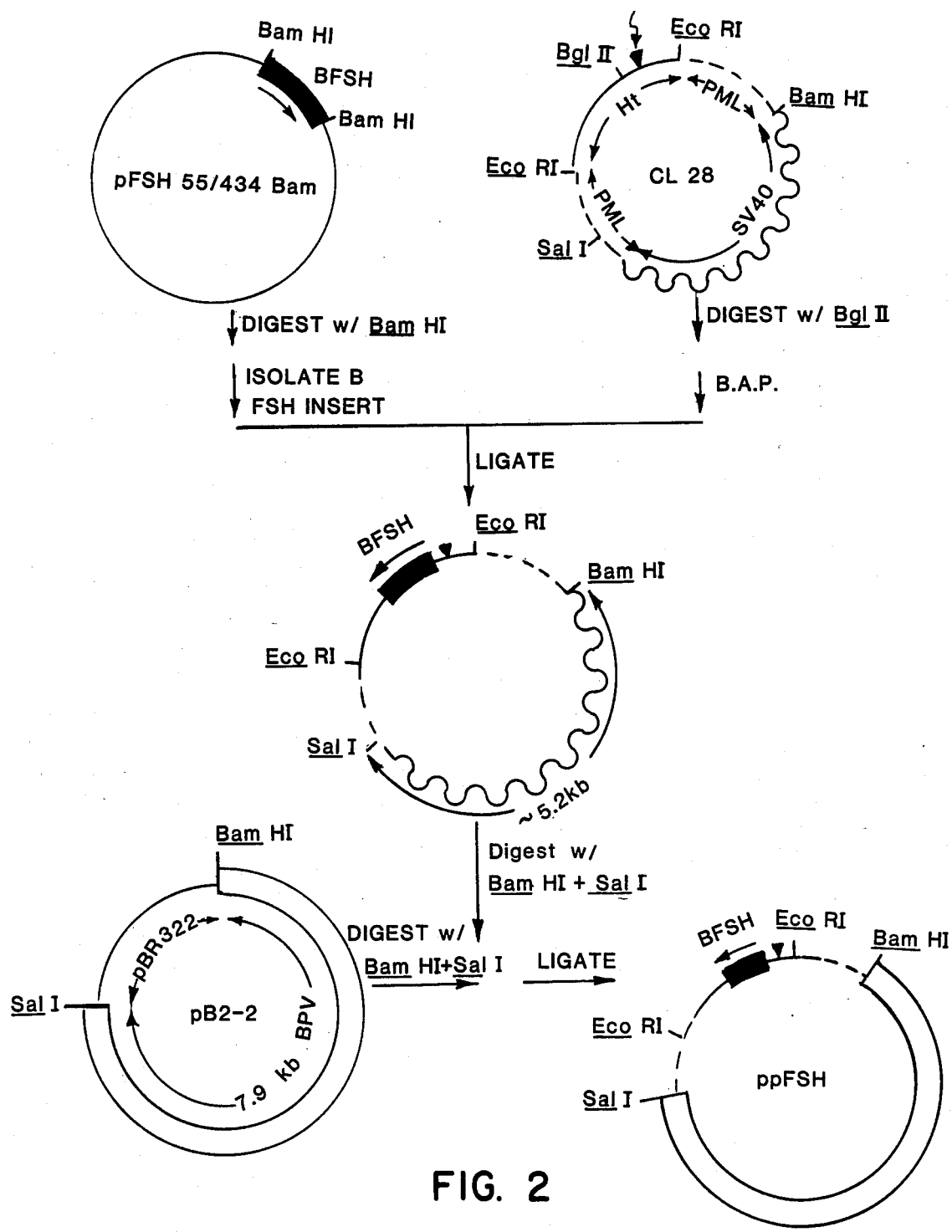
FIG. 2 is a diagrammatic representation of a procedure for inserting the porcine beta FSH gene into an expression vector.

Referring to FIG. 2, the porcine beta FSH cDNA sequence can, for example, be inserted into a bovine papilloma virus (BPV) expression vector in which the cDNA sequence is under the control of the mouse metallothionein (MMT) promoter. The first step in this procedure will be to cut the cDNA out of pBR322 using PstI and SacI, which will cut at the 5' end just downstream from the ATG, and at the 3' end, downstream from the end of the coding region (see restriction map, above). A synthetic sequence will be added to the 5' end, which will complete the gene up to ATG and contain a BamHI overhang. At the 3' end, the SacI overhang will be made blunt and a BamHI linker will be attached. The modified sequence will be inserted into pBR322 at the Bam site to form plasmid pFSH 55/434 Bam (FIG. 2).

Next, the plasmid CL28 (identical to plasmid JYMMT(E); Hamer et al. (1983) J. Mol. Applied Gen. 1, 273–288), containing the murine metallothionein promoter, SV40 DNA, and the pBR322 sequences, is cut with the restriction endonuclease BglII. At this site is inserted the FSH cDNA, containing an untranslated region at the 3' end.

The resulting plasmid is digested with the restriction enzymes BamHI and SalI to release the SV40 DNA sequences.

Plasmid pB2-2, which contains the entire BPV genome, and some pBR322 sequences, is digested with BamHI and SalI to yield the BPV genome with BamHI/SalI ends; this fragment is ligated into the above plasmid containing the metallothionein-FSH sequences, to form expression plasmid ppFSH, as shown.

Plasmid ppFSH can then be used to transform mammalian host cells, and porcine beta FSH can be isolated and purified, according to conventional methods.

USE

The porcine beta FSH can be used to produce anti-beta FSH antibodies, using conventional methods, which can be labeled and used in radioimmunoassays of biological fluids of pigs and other animals, as well as humans, for beta FSH. Measuring beta FSH levels can be important in the diagnosis, monitoring, and characterization of pituitary tumors and other pituitary malfunctions.

The porcine beta FSH of the invention can also be used, alone or in combination with alpha FSH, to induce superovulation in farm animals, e.g., pigs, cattle, horses, sheep, and goats. Alpha FSH (bovine) has been cloned and sequenced and described in Erwin et al. (1983) Biochemistry 22, 4856. FSH is also available commercially, e.g. from the Reheis division of Armour Pharmaceutical Company, Kankakee, IL., and the alpha subunit could be obtained from the commercial dimer. Beta and alpha FSH can associate into the dimeric form spontaneously, with no special reaction conditions being required. Also, the species from which the two subunits are derived may not need to be the same for the formation of a functional dimer.

Other uses of porcine FSH are the treatment, in animals, of genital infantilism, gonadal regression, incomplete follicular development, persistent luteal cysts, aspermia, and infertility.

The porcine beta FSH of the invention can be administered to animals according to established FSH administration techniques and dosages, whether administered alone or in the form of a dimer with alpha FSH. Beta FSh alone can be effective because the pituitary normally overproduces the alpha subunit, which is available for dimer formation with beta FSH in vivo.

Other embodiments are with the following claims.

TABLE 1

```
                                                 82                                                           112
GTA CTT TCA CGG TCT CGT ACA CCA GCT CCT TAA TTG TTT GGT TTC CAC CCC AAG  ATG  AAG
                                                                          Met  Lys

172
TCG CTG CAG TTT TGC TTC CTA TTC TGT TGC TGG AAA GCC ATC TGC TGC AAT AGC  TGT  GAG
Ser Leu Gln Phe Cys Phe Leu Phe Cys Cys Trp Lys Ala Ile Cys Cys Asn Ser  Cys  Glu 202                                                           232
CTG ACC AAC ATC ACC ATC ACA GTG GAG AAA GAG GAG TGT AAC TTC TGC ATA AGC ATC AAC
Leu Thr Asn Ile Thr Ile Thr Val Glu Lys Glu Glu Cys Asn Phe Cys Ile Ser Ile Asn
```

TABLE 1-continued

```
                 262                                                          292
ACC ACG TGG TGT GCT GGC TAT TGC TAC ACC CGG GAC CTG GTA TAC AAG GAC CCA GCC AGG
Thr Thr Trp Cys Ala Gly Tyr Cys Tyr Thr Arg Asp Leu Val Tyr Lys Asp Pro Ala Arg 322                                                          252
CCC AAC ATC CAG AAA ACA TGT ACC TTC AAG GAG CTG GTG TAC GAG ACC GTG AAA GTA CCT
Pro Asn Ile Gln Lys Thr Cys Thr Phe Lys Glu Leu Val Tyr Glu Thr Val Lys Val Pro 382                                                          412
GGC TGT GCT CAC CAT GCA GAC TCC CTG TAT ACG TAT CCA GTA GCC ACC GAA TGT CAC TGT
Gly Cys Ala His His Ala Asp Ser Leu Tyr Thr Tyr Pro Val Ala Thr Glu Cys His Cys 442                                                          472
GGC AAG TGT GAC AGT GAC AGT ACT GAC TGC ACC GTG AGA GGC CTG GGG CCC AGC TAC TGC
Gly Lys Cys Asp Ser Asp Ser Thr Asp Cys Thr Val Arg Gly Leu Gly Pro Ser Tyr Cys 502                                                          532
TCC TTC AGT GAA ATG AAA GAA TAA  AGA GCA GTG GAC ATT TCA TGC TTC CTA CCC TTG TCT
Ser Phe Ser Glu Met Lys Glu End 562                                                          592
GAA GGA CCA AGA CGT CCA AGA AGT TTG TGT GTA CAT GTG CCC AGG CTG CAA ACC ACT ATG 622                                                          652
AGA GAC CCC ACT GAT CCC TGC TGT CCT GTG GAG GAG GAG CTC GAG GAA TGC AGA GTG CTA 682                                                          712
GGG CCT CAG TCC CAT CAC CAC TCA ACC CTG TAT TTT GGG TCT GGT TCC ATA AGT TTT ATT 742                                                          772
CGG TCT TTT TTT TTT AAA TTA CTC AAT GAA TTT TAT TAC ATT TAT AAT TGT AGC AAG GAT

CAT CAC AA
```

TABLE 2

```
         62         72         82         92        102        112
CTACTTTCAC GGTCTCGTAC ACCAGCTCCT TAATTGTTTG GTTTCCACCC CAAC ATG  AAG
   R           R          A
   S           S          L
   A           A          U
   1           1          1

122        132        142        152        162        172
TCGCTGCAGT TTTGCTTCCT ATTCTGTTGC TGGAAAGCCA TCTGCTGCAA TAGCTGTGAG
   S P                                  S          A          A
   B S                                  B          L          L
   V T                                  V          U          U
   1 1                                  1          1          1

182        192        202        212        222        232
CTGACCAACA TCACCATCAC AGTGGAGAAA GAGGAGTGTA ACTTCTGCAT AAGCATCAAC
         H                     M                              S
         P                     N                              F
         H                     L                              A
         1                     1                              1

242        252        262        272        282        292
ACCACGTGGT GTGCTGGCTA TTGCTACAC C CGGGACCTGG TATACAAGGA CCCAGCCAGG
                        S N   A  B   S         A        B   S
                        M C   V  S   N         V        S   A
                        A I   A  T   A         A        I   U
                        1 1   2  1   1         2        1   1

302        312        322        332        342        352
CCCAACATCC AGAAAACATG TACCTTCAAG GAGCTGGTGT ACGAGACCGT GAAAGTACCT
     F       A   R           A       R            R  B
     O       F   S           L       S            S  S
     K       L   A           U       A            A  T
     1       3   1           1       1            1  1

362        372        382        392        402        412
GGCTGTGCTC ACCATGCAGA CTCCCTGTAT ACGTATCCAG TAGCCACCGA ATGTCACTGT
     H  H              H          S
     B  P              I          N
     I  H              N          A
     1  1              1          1
```

TABLE 2-continued

```
       422        432        442        452        462        472
GGCAAGTGTG ACAGTGACAG TACTGACTGC ACCGTGAGAG GCCTGGGGCC CAGCTACTGC
           R R                  M S H  B    A S        A
           R S                  N T A  S    P A        L
           U A                  L U E  T    A U        U
           1 1                  1 1 3  1    1 1        1

482        492        502        512        522        532
TCCTTCAGTG AAATGAAAGA ATAAAGAGCA GTGGACATTT CATGCTTCCT ACCCTTGTCT 542        552        562        572        582        592
GAAGGACCAA GACGTCCAAG AAGTTTGTGT GTACATGTGC CCAGGCTGCA AACCACTATG
  A          A                    R A       B            B
  V          A                    S F       S            S
  A          T                    A L       T            V
  2          2                    1 3       1            1

602        612        622        632        642        652
AGAGACCCCA CTGATCCCTG CTGTCCTGTG GAGGAGGAGC TCCAGGAATG CAGAGTGCTA
           B                     M M  S A   B
           I                     N N  A L   S
           N                     L L  C U   T
           1                     1 1  1 1   1

662        672        682        692        702        712
GGGC CTCAGT CCCATCACCA CTCAACCCTG TATTTTGGGT CTGGTTCCAT AAGTTTTATT
S H  M D                M
A A  N D                P
U E  L E                N
1 3  1 1                1

722        732        742        752        762        772
CGGTCTTTTT TTTTTAAATT ACTCAATGAA TTTTATTACA TTTATAATTG TAGCAAGGAT
            A                                              B S
            N                                              I A
            A                                              N U
            3                                              1 A

CATCACAA
```

TABLE 3

| Amino Acid Number | Closset et al. | Porcine beta FSH encoded by cDNA of invention |
|---|---|---|
| 2 | Glx | Glu |
| 11 | Glx | Glu |
| 12 | Val | Lys |
| 13 | Lys | Glu |
| 14 | Cys | Glu |
| 15 | Leu | Cys |
| 16 | Thr | Asn |
| 31 | Thr | Tyr |
| 33 | Gly | — |
| 35 | Asx | Asp |
| 40 | Asx | Asp |
| 45 | Asx | Asn |
| 47 | Glx | Gln |
| 52 | Tyr | Phe |
| 53 | Arg | Lys |
| 54 | Glx | Glu |
| 58 | Glx | Glu |
| 70 | Asx | Asp |
| 80 | Glx | Glu |
| 87 | Asx | Asp |
| 89 | Asx | Asp |
| 92 | Asx | Asp |
| 106 | Gly | Ser |
| 108–110 | — | Met—Lys—Glu |

I claim:

1. A cDNA sequence encoding porcine beta FSH.
2. A vector comprising a DNA sequence encoding porcine beta FSH.
3. The vector of claim 2, said vector being a plasmid.

* * * * *